United States Patent [19]

Nyce

[11] Patent Number: 5,527,789
[45] Date of Patent: Jun. 18, 1996

[54] METHOD OF INHIBITING CARCINOGENESIS BY TREATMENT WITH DEHYDROEPIANDROSTERONE AND ANALOGS THEREOF

[75] Inventor: Jonathan W. Nyce, Greenville, N.C.

[73] Assignee: East Carolina University, Greenville, N.C.

[21] Appl. No.: 284,307

[22] Filed: Aug. 2, 1994

Related U.S. Application Data

[63] Continuation of Ser. No. 840,510, Feb. 24, 1992, abandoned.

[51] Int. Cl.$^6$ .......................... A61K 31/56; A61K 31/665; A61K 31/66; A61K 31/56; A61K 31/58
[52] U.S. Cl. ..................... 514/178; 514/99; 514/102; 514/121; 514/171; 514/172; 514/690
[58] Field of Search ............................ 514/178, 690, 514/99, 121, 102, 172, 171

[56] References Cited

U.S. PATENT DOCUMENTS

| | | | |
|---|---|---|---|
| 4,956,355 | 9/1990 | Prendergast | 514/178 |
| 5,001,119 | 3/1991 | Schwartz et al. | 514/177 |

FOREIGN PATENT DOCUMENTS

| | | | |
|---|---|---|---|
| 0429187 | 5/1991 | European Pat. Off. | 514/178 |
| 2240472 | 8/1991 | United Kingdom | 514/178 |
| WO91/04030 | 4/1991 | WIPO | 514/178 |

OTHER PUBLICATIONS

M. Abou–Gharbia et al., *J. Pharm. Sci.* 70, No. 10, 1154–1157 (1981).
K. Folkers et al., *Proc. Natl. Acad. Sci. USA* 87, 8931–8934 (1990).
S. Greenberg and W. Frishman, *J. Clin. Pharmacol.* 30, 596–608 (1990).
S. Mortensen et al., *Int. J. Tiss. Reac.* XII, No. 3, 155–162 (1990).
J. Nyce et al., *Carcinogensis* 5, No. 1, 57–62 (1984).
S. Schulz and J. Nyce, *Cancer Research* 51, 6563–6567 (1991).

*Primary Examiner*—Jerome D. Goldberg
*Attorney, Agent, or Firm*—Bell, Seltzer, Park & Gibson

[57] ABSTRACT

A method of combatting cancer in a subject comprising administering to said subject dehydroepiandrosterone (DHEA) or an analog thereof in an amount effective to combat cancer is disclosed in which heart failure induced by the DHEA or analog thereof is combatted by administering to the subject a ubiquinone, in an amount effective to combat heart failure induced by the DHEA or analog thereof.

A prefered DHEA analog for carrying out the invention is 16 alpha-fluoroepiandrosterone, and a preferred ubiquinone for carrying out the invention is Coenzyme $Q_{10}$.

19 Claims, 8 Drawing Sheets

METHOD OF INHIBITING CARCINOGENESIS BY TREATMENT WITH DEHYDROEPIANDROSTERONE AND ANALOGS THEREOF

This is a continuation of application Ser. No. 07/840,510 filed on 24 Feb. 1992, now abandoned.

FIELD OF THE INVENTION

The present invention relates to a method for combatting cancer by administering dehydroepiandrosterone (DHEA) or an analog thereof in combination with a ubiquinone, wherein the ubiquinone is administered in an amount effective to combat heart failure.

BACKGROUND OF THE INVENTION

DHEA is a naturally occurring steroid secreted by the adrenal cortex with apparent chemoprotective properties. Epidemiological research has shown that low endogenous levels of the natural steroid dehydroepiandrosterone (DHEA) correlate with increased risk of developing some forms of cancer, such as premenopausal breast cancer in women and bladder cancer in both sexes. R. D. Bulbrook et al., *Lancet* 2, 395–398 (1971); B. Zumoff, et al., *Cancer Res.* 41, 3360–3363 (1981); G. B. Gordon, *Cancer Res.* 51, 1366–1369 (1991); K. J. Helzlsouer, *Cancer. Res.* 52, 1–5 (1992). The ability of DHEA and DHEA analogs to inhibit carcinogenesis is believed to result from their uncompetitive inhibition of the activity of the enzyme glucose-6-phosphate dehydrogenase (G6PDH).

G6PHD is the rate limiting enzyme of the hexose monophosphate pathway, a major source of intracellular ribose-5-phosphate and NADPH. P. A. Marks et al., *Proc. Nat. Acad. Sci. USA* 46, 447–452 (1960). Ribose-5-phosphate is a necessary substrate for the synthesis of both ribo- and deoxyribonucleotides required for the synthesis of RNA and DNA. NADPH is a cofactor also involved in nucleic acid biosynthesis and the synthesis of hydroxmethylglutaryl Coenzyme A reductase (HMG CoA reductase). S. Schulz et al., Inhibition of Protein Isoprenylation and p21ras Membrane Association by DHEA in Human Colonic Adenocarcinoma Cells in Vitro, *Cancer Res.* (Dec. 15, 1991).

HMG CoA reductase is a very unusual enzyme in that it requires two moles of NADPH for each mole of product, mevalonate, produced. Thus, it appears that HMG CoA reductase would be ultrasensitive to DHEA-mediated NADPH depletion, and that DHEA-treated cells would rapidly show depletion of intracellular pools of mevalonate. Mevalonate is required for DNA synthesis, and DHEA arrests human cells in the G1 phase of the cell cycle in a manner closely resembling that of the direct HMG CoA reductase inhibitor lovastatin. S. Schulz et al, Mechanism of Cell Growth Inhibition and Cell Cycle Arrest in Human Colonic Adenocarcinoma Cells by DHEA: Role of Isoprenoid Biosynthesis, *Cancer Res.* (submitted). Because G6PDH produces mevalonic acid used in cellular processes such as protein isoprenylation and the synthesis of dolichol (a precursor for glycoprotein biosynthesis), DHEA inhibits carcinogenesis by depleting mevalonic acid and thereby inhibiting protein isoprenylation and glycoprotein synthesis.

Mevalonate is the central precursor for the synthesis of cholesterol, as well as for the synthesis of a variety of nonsterol compounds involved in posttranslational modification of proteins (farnesyl pyrophosphate and geranlygeranyl pyrophosphate); for dolichol, which is required for the synthesis of glycoproteins involved in cell-to-cell communication and cell structure; and for ubiquinone, an antioxidant with an established role in cellular respiration. P. Mitchell, *Annals of the N.Y. Acad. Sci.* 341, 564 (1980); M. Gutman, *Biochem. Biophys. Acta.* 594, 53 (1980).

Adequate ubiquinone is essential for maintaining proper cardiac function and the addition of exogenous ubiquinone has recently been shown to have beneficial effect in patients with chronic heart failure. S. Greenberg et al., *J. Clin. Pharmacol.* 30, 596–608 (1990); S. A. Mortensen et al., *Int. J. Tiss. Reac.* 12(3), 155–162 (1990). Additionally, ubiquinone has been shown to be depleted in humans and animals treated with the direct HMG CoA reductase inhibitor lovastatin. K. Folkers et al., *Proc. Nat. Acad. Sci. USA* 87, 8931–8934 (1990); R. A. Willis et al., *Proc. Nat. Acad. Sci. USA* 87, 8928–8930 (1990). Such lovastatin-induced depletion of ubiquinone has been shown to lead to chronic heart failure (or to upgrading of low heart failure into life-threatening high grade heart failure). K. Folkers et al., *Proc. Nat. Acad. Sci. USA* 87, 8931–8934 (1990).

DHEA, unlike lovastatin, inhibits HMG CoA reductase indirectly by inhibiting G6PDH and depleting NADPH, a required cofactor for HMG CoA reductase. However, DHEA indirectly inhibits HMG CoA reductase sufficiently to deplete intracellular mevalonate. S. Schulz et al., Inhibition of Protein Isoprenylation and p21ras Membrane Association by DHEA in Human Colonic Adenocarcinoma Cells in Vitro, *Cancer Res.* (Dec. 15, 1991). This, too, will lead to ubiquinone depletion and consequent chronic heart failure following long term usage.

Thus although DHEA was once considered a safe drug, it is now predicted that with long term administration of DHEA or its analogs, chronic heart failure occurs as a complicating side effect. Further, some analogs of DHEA produce this side effect to a greater extent in that specific analogs have been reported to be a more potent inhibitor of G6PDH than DHEA.

SUMMARY OF THE INVENTION

A first aspect of the present invention is a method of combatting cancer, wherein dehydroepiandrosterone (DHEA) or an analog thereof is administered to the subject in an amount effective to combat cancer, and wherein a ubiquinone is administered to the subject in an amount effective to combat heart failure induced by the DHEA or analog thereof. In an embodiment of the invention, the dehydroepiandrosterone or analog thereof is represented by the formula:

wherein:

R is hydrogen or a halogen; and $R^1$ is hydrogen or an SO2OM group where M is hydrogen, sodium, a sulphatide group a phosphatide group $$-\underset{\underset{O}{\|}}{\overset{\overset{O}{\|}}{P}}-OCH_2\underset{OCOR^2}{\overset{|}{C}H}CH_2OCOR^3$$

wherein each of $R^2$ and $R^3$, which may be the same of different, is a straight or branched chain alkyl radical of 1 to 14 carbon atoms, or a glucuronide group

[structure: sugar ring with COOH, O, OH, HO substituents]

and the broken line represents an optional double bond, and the hydrogen atom at position 5 is present in the alpha or beta configuration or the compound comprises a mixture of both configurations; and the ubiquinone is represented by the formula:

[structure (II): quinone ring with CH_3O, CH_3O, O, O, CH_3, and (CH_2CH=CCH_2)_n—H side chain with CH_3]

wherein n=1 to 10. Preferably, R is a halogen, $R^1$ is hydrogen, and the double bond is present, and n is an integer from 6 to 10. More preferably the dehydroepiandrosterone or analog thereof is 16-alpha-fluoroepiandrosterone, and n is 10.

A second aspect of the present invention is a pharmaceutical formulation comprising DHEA or an analog thereof in an amount effective to combat cancer and a ubiquinone in an amount effective to combat heart failure together in a pharmaceutically acceptable carrier.

A third aspect of the present invention is the use of ubiquinone for the preparation of a medicament for combatting heart failure in a patient undergoing cancer-combatting treatment with DHEA or an analog thereof.

BRIEF DESCRIPTION OF THE DRAWINGS

In the drawings which form a portion of the disclosure of the invention.

DETAILED DESCRIPTION OF THE INVENTION

In the present invention, DHEA or an analog thereof is administered to a subject in an amount effective to combat cancer concurrently with a ubiquinone in an amount effective to combat heart failure. DHEA (dehydroisoandrosterone) is known (Merck Index Monograph No. 7710). Numerous DHEA analogs are also known. See, e.g., U.S. Pat. No. 4,956,355, UK Patent No. 2,240,472, EPO patent application Ser. No. 429,187 and PCT patent application Ser. No. 91/04030, the disclosures of which are to be incorporated herein by reference. Illustrative of DHEA and its analogs in accordance with the invention are compounds represented by the formula:

[structure (I): steroid skeleton with H_3C, CH_3, R^1O, and R substituent]

wherein:

R is hydrogen or a halogen (e.g., bromine, fluorine or chlorine);

$R^1$ is hydrogen or an $SO_2OM$ group where M is hydrogen, sodium, a sulphatide group $$-SO_2O-CH_2\underset{OCOR^2}{\overset{|}{C}H}CH_2OCOR^3$$

a phosphatide group $$-\underset{\underset{O}{\|}}{\overset{\overset{O}{\|}}{P}}-OCH_2\underset{OCOR^2}{\overset{|}{C}H}CH_2OCOR^3$$

wherein each of $R^2$ and $R^3$, which may be the same of different, is a straight or branched chain alkyl radical of 1 to 14 carbon atoms, or a glucuronide group

[structure: sugar ring with COOH, O, OH, HO substituents]

and wherein the broken line represents an optional double bond, and the hydrogen atom at position 5 is present in the alpha or beta configuration or the compound comprises a mixture of both configurations.

Compounds illustrative of Formula (I) above include: DHEA wherein R and $R^1$ are each hydrogen and the double bond is present; 16 alpha-bromoepiandrosterone wherein R is Br, $R^1$ is H, and the double bond is present; 16 alpha-fluoroepiandrosterone wherein R is F, $R^1$ is H and the double bond is present; etiocholanolone wherein R and $R^1$ are each hydrogen and the double bond is absent; dehydroepiandrosterone sulphate wherein R is H, $R^1$ is $SO_2OM$, and M is Na, and the double bond is absent; and dehydroepiandrosterone sulphatide wherein R is H, $R^1$ is $SO_2OM$ and M is a sulphatide group as defined above, and the double bond is absent. Preferably the DHEA or DHEA analog is a halogenated DHEA analog according to Formula I wherein R is Br, F, or Cl and $R^1$ is H and the double bond is present, and most preferably wherein R is F and $R^1$ is H and the double bond is present.

The compounds of Formula I are made in accordance with known procedures, or variations thereof, which will be apparent to those skilled in the art. See U.S. Pat. No. 4,956,355, UK Patent No. 2,240,472, EPO patent application Ser. No. 429,187 and PCT patent application Ser. No.

91/04030. See also M. Abou-Gharbia et al., *J. Pharm. Sci.* 70, 1154–1157 (1981), also incorporated herein by reference.

The ubiquinone compound is a structure based on a 2,3-dimethoxy-5-methylbenzoquinone nucleus with a variable terpenoid acid chain containing one to twelve monounsaturated trans-isoprenoid units. Such compounds are known in the art as "Coenzyme $Q_n$," in which n equals 1 to 12. These compounds are also known in the art as "ubiquinone(x)," in which x designates the total number of carbon atoms in the side chain and can be any multiple of 5. The ubiquinone compounds of the present invention are referred to herein as compounds represented by the formula:

wherein n=1 to 10. Preferably, in the method of the invention, the ubiquinone is a compound according to Formula II, wherein n=6 to 10 (e.g., Coenzymes $Q_{6-10}$), and most preferably n=10 (e.g., Coenzyme $Q_{10}$).

The phrase "concurrently administering," as used herein, means that DHEA or the DHEA analog and the ubiquinone are administered either (a) simultaneously in time (optionally by formulating the two together in a common carrier), or (b) at different times during the course of a common treatment schedule. In the latter case, the two compounds are administered at times sufficiently close for the ubiquinone to counterbalance the deterioration of the heart function resulting from the administration of DHEA or its analog.

Subjects to be treated by the method of the present invention include both human and animal (e.g., dog, cat, cow, horse) subjects, and are preferably mammalian subjects.

The active compounds (i.e., the ubiquinone and the DHEA or analog thereof) may be administered to the subject by any suitable means, such as orally, topically (including transdermally), or parenterally (e.g., by intraperitoneal, intraveneous, subcutaneous, or intramuscular injection), and in dosages known in the art. See, e.g., U.S. Pat. No. 4,956,355, UK Patent No. 2,240,472, EPO patent application Ser. No. 429,187, and PCT patent application Ser. No. 91/04030, which are incorporated by reference above. See also S. A. Mortensen et al., *Int. J. Tiss. Reac. XII*(3), 155–162 (1990), S. Greenberg et al., *J. Clin. Pharm.* 30, 596–608 (1990), and K. Folkers, et al., *Proc. Nat'l. Acad. Sci.* 87, 8931–8934 (1990), also incorporated herein by reference.

Note that the DHEA or analog thereof may or may not be administered for a time sufficient to deplete endogenous ubiquinone. If the DHEA or analog thereof is administered for a time sufficient to deplete endogenous ubiquinone, then the administration of exogenous ubiquinone replenishes the level of ubiquinone. If the DHEA or analog thereof is administered for a time sufficient to deplete endogenous ubiquinone, then the administration of exogenous ubiquinone offsets future depletion.

In general, the ubiquinone is administered in an amount effective to combat heart failure, and the dosage will vary depending upon the condition of the subject and the route of administration. The ubiquinone is preferably administered in a total amount per day of about 1 to 1200 mg/kg body weight, more preferably about 30 to 600 mg/kg, and most preferably about 50 to 150 mg/kg. The ubiquinone may be administered once or several times a day.

The DHEA or DHEA analog is, in general, administered in an amount effective to combat cancer, and the dosage will likewise vary depending upon the condition of the subject and the route of administration. The DHEA or DHEA analog is preferably administered in a total amount per day of about 1 to 3600 mg/kg body weight, more preferably about 5 to 1800 mg/kg, and most preferably about 20 to 100 mg/kg. The DHEA or DHEA analog may be administered once or several times a day.

The compounds of Formula I may be administered per se or in the form of a pharmaceutically acceptable salt. When used in medicine, the salts of the compounds of Formula (I) should be both pharmacologically and pharmaceutically acceptable, but non-pharmaceutically acceptable salts may conveniently be used to prepare the free active compound or pharmaceutically acceptable salts thereof and are not excluded from the scope of this invention. Such pharmacologically and pharmaceutically acceptable salts include, but are not limited to, those prepared from the following acids: hydrochloric, hydrobromic, sulphuric, nitric, phosphoric, maleic, acetic, salicylic, p-toluenesulfonic, tartaric, citric, methanesulphonic, formic, malonic, succinic, naphthalene-2-sulphonic and benzenesulphonic. Also, pharmaceutically acceptable salts can be prepared as alkaline metal or alkaline earth salts, such as sodium, potassium or calcium salts of the carboxylic acid group. Thus, the present invention also provides pharmaceutical formulations, both for veterinary and for human medical use, which comprise the ubiquinone together with one or more pharmaceutically acceptable carriers thereof and optionally any other therapeutic ingredients. The carrier(s) must be pharmaceutically acceptable in the sense of being compatible with the other ingredients of the formulation and not unduly deleterious to the recipient thereof.

Pharmaceutical formulations of the present invention may optionally include DHEA or DHEA analogs, preferably as described above. Such a formulation is useful for concurrently administering DHEA or a DHEA analog and the ubiquinone in a method as described above.

The formulations include those suitable for oral, rectal, topical, transdermal, nasal, ophthalmic or parenteral (including subcutaneous, intramuscular and intravenous) administration. Formulations suitable for oral and parenteral administration are preferred.

The formulations may conveniently be presented in unit dosage form and may be prepared by any of the methods well known in the art of pharmacy. All methods include the step of bringing the active compound into association with a carrier which constitutes one or more accessory ingredients. In general, the formulations are prepared by uniformly and intimately bringing the active compound into association with a liquid carrier, a finely divided solid carrier, or both, and then, if necessary, shaping the product into desired formulations.

Formulations of the present invention suitable for oral administration may be presented as discrete units such as capsules, cachets, tablets or lozenges, each containing a predetermined amount of the potentiating agent as a powder or granules; or a suspension in an aqueous liquor or non-aqueous liquid such as a syrup, an elixir, an emulsion or a draught.

A tablet may be made by compression or molding, optionally with one or more accessory ingredients. Compressed tablets may be prepared by compressing in a suitable machine, with the active compound being in a free-flowing form such as a powder or granules which is optionally mixed with a binder, disintegrant, lubricant, inert diluent, surface active agent or dispersing agent. Molded tablets comprised of a mixture of the powdered active compound with a suitable carrier may be made by molding in a suitable machine.

A syrup may be made by adding the active compound to a concentrated aqueous solution of a sugar, for example sucrose to which may also be added any accessory ingredient(s). Such accessory ingredient(s) may include flavorings, suitable preservatives, an agent to retard crystallization of the sugar, and an agent to increase the solubility of any other ingredient, such as a polyhydric alcohol, for example glycerol or sorbitol.

Formulations suitable for parenteral administration conveniently comprise a sterile aqueous preparation of the active compound, which is preferably isotonic with the blood of the recipient.

Nasal spray formulations comprise purified aqueous solutions of the active compound with preservative agents and isotonic agents. Such formulations are preferably adjusted to a pH and isotonic state compatible with the nasal mucous membranes.

Formulations for rectal administration may be presented as a suppository with a suitable carrier such as cocoa butter, or hydrogenated fats or hydrogenated fatty carboxylic acids.

Ophthalmic formulations are prepared by a similar method to the nasal spray, except that the pH and isotonic factors are preferably adjusted to match that of the eye.

Topical formulations comprise the active compound dissolved or suspended in one or more media such as mineral oil, petroleum, polyhydroxy alcohols or other bases used for topical pharmaceutical formulations. The addition of other accessory ingredients, vide infra, may be desirable.

In addition to the aforementioned ingredients, the formulations of this invention may further include one or more accessory ingredient(s) selected from diluents, buffers, flavoring agents, binders, disintegrants, surface active agents, thickeners, lubricants, preservatives (including antioxidants) and the like.

The following Examples are provided to illustrate the present invention, and should not be construed as limiting thereof.

Example 1

Preparation of the Experimental Model

Cell cultures. HT-29 SF cells, which represent a subline of HT-29 cells (ATCC, Rockville, Md.) and are adapted for growth in completely defined serum-free PC-1 medium (Ventrex, Portland, Me.), were obtained. Stock cultures were maintained in this medium at 37° C. in a humidified atmosphere containing 5% $CO_2$. At confluence cultures were replated after dissociation using trypsin/EDTA (Gibco, Grand Island, N.Y.) and re-fed every 24 hours. Under these conditions, the doubling time for HT-29 SF cells during logarithmic growth was 24 hours.

Flow Cytometry. Cells were plated at $10^5$/60-mm dish in duplicate. For analysis of cell cycle distribution, cultures were exposed to either 0, 25, 50, or 200 µM DHEA. For analysis of reversal of cell cycle effects of DHEA, cultures were exposed to either 0 or 25 µM DHEA, and the media were supplemented with MVA, CH, RN, MVA plus CH, or MVA plus CH plus RN or were not supplemented. Cultures were trypsinized following 0, 24, 48, or 74 hours and fixed and stained using a modification of a procedure of Bauer et al., *Cancer Res.*, 46, 3173–3178 (1986). Briefly, cells were collected by centrifugation and resuspended in cold phosphate-buffered saline. Cells were fixed in 70% ethanol, washed, and resuspended in phosphate-buffered saline. One ml hypotonic stain solution [50 µg/ml propidium iodide (Sigma Chemical Co.), 20 µg/ml RNase A (Boehringer Mannheim, Indianapolis, Ind.), 30 mg/ml polyethylene glycol, 0.1% Triton X-100 in 5 mM citrate buffer] was then added, and after 10 min at room temperature, 1 ml of isotonic stain solution [propidium iodide, polyethylene glycol, Triton X-100 in 0.4M NaCl] was added and the cells were analyzed using a flow cytometer, equipped with pulse width/pulse area doublet discrimination (Becton Dickinson Immunocytometry Systems, San Jose, Calif.). After calibration with fluorescent beads, a minimum of $2 \times 10^4$ cells/sample were analyzed, data were displayed as total number of cells in each of 1024 channels of increasing fluorescence intensity, and the resulting histogram was analyzed using the Cellfit analysis program (Becton Dickinson).

Example 2

Analysis of Growth Inhibition and Cell Cycle Arrest by DHEA

Growth Inhibition Assay. Cells were plated 25,000 cells/30-mm dish in quadruplicate, and after 2 days received 0, 12.5, 25, 50, or 200 µM DHEA. Cell number was determined 0, 24, 48, and 72 hours later using a Coulter counter (model $Z_f$; Coulter Electronics, Inc., Hialeah, Fla.). DHEA (AKZO, Basel, Switzerland) was dissolved in dimethyl sulfoxide, filter sterilized, and stored at −20° C. until use.

Figure 1:
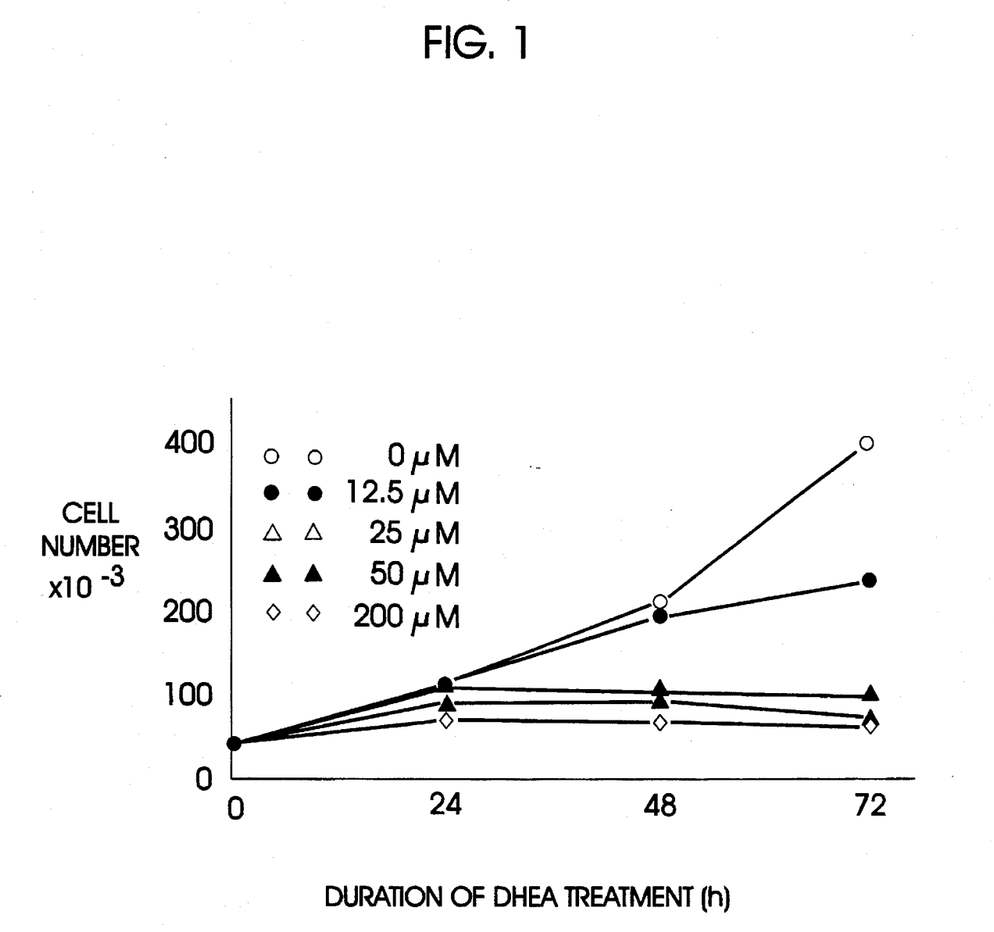
FIG. 1 illustrates the inhibition of HT-29 SF cells by DHEA.

FIG. 1 illustrates the inhibition of growth for HT-29 cells by DHEA. Points refer to numbers of cells, and bars refer to SEM. Each data point was performed in quadruplicate, and the experiment was repeated three times. Where SEM bars are not apparent, SEM was smaller than symbol. Exposure to DHEA resulted in a reduced cell number compared to controls after 72 hours in 12.5 µM, 48 hours in 25 or 50 µM, and 24 hours in 200 µM DHEA, indicating that DHEA produced a time- and dose-dependent inhibition of growth.

Figure 2A:
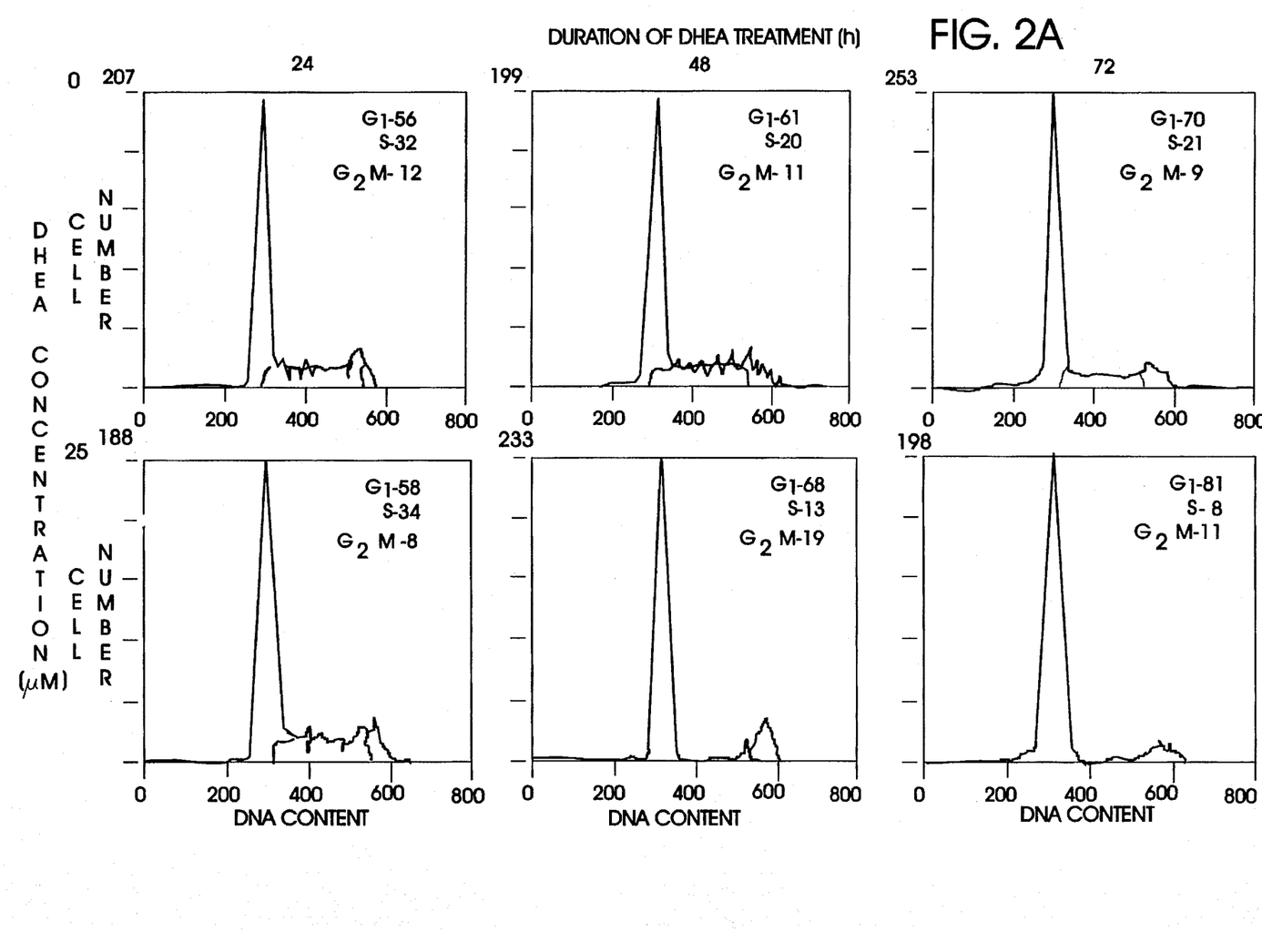
FIG. 2 illustrates the effects of DHEA on cell cycle distribution in HT-29 SF cells.
Figure 2B:
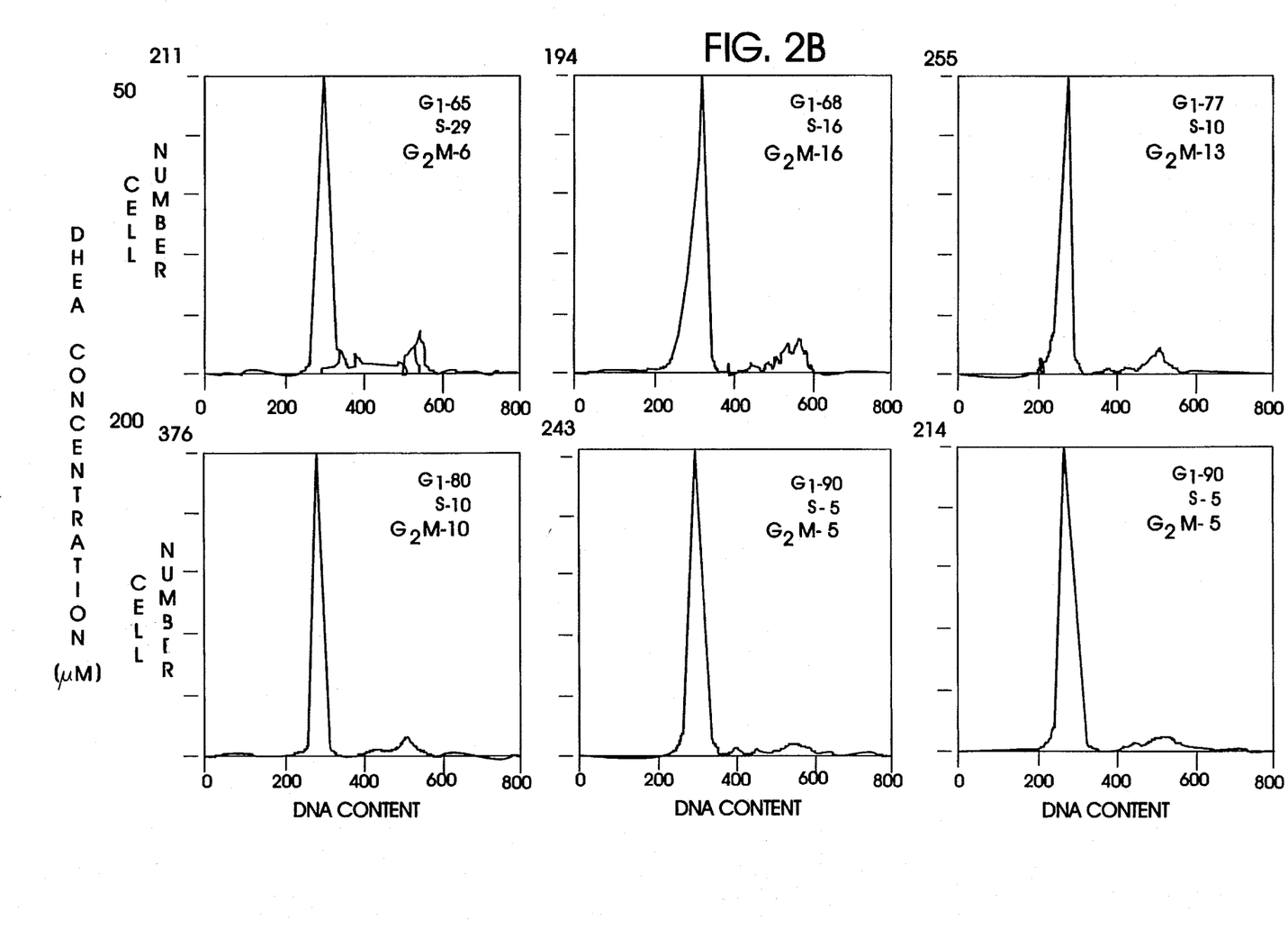

Cell Cycle Arrest by DHEA. To examine the effects of DHEA on cell cycle distribution, HT-29 SF cells were plated ($10^5$ cells/60 mm dish), and 48 hours later treated with 0, 25, 50, or 200 µM DHEA. FIG. 2 illustrates the effects of DHEA on cell cycle distribution in HT-29 SF cells. After 24, 48, and 72 hours, cells were harvested, fixed in ethanol, and stained with propidium iodide, and the DNA content/cell was determined by flow cytometric analysis. The percentage of cells in $G_1$, S, and $G_2M$ phases was calculated using the Cellfit cell cycle analysis program. S phase is marked by a quadrangle for clarity. Representative histograms from duplicate determinations are shown. The experiment was repeated three times.

The cell cycle distribution in cultures treated with 25 or 50 µM DHEA was unchanged after the initial 24 hours. However, as the time of exposure to DHEA increased, the proportion of cells in S phase progressively decreased, and the percentage of cells in $G_1$ phase was increased after 72 hours. A transient increase in $G_2M$ phase cells was apparent after 48 hours. Exposure to 200 µM DHEA produced a similar but more rapid increase in the percentage of cells in $G_1$ and a decreased proportion of cells in S phase after 24 hours, which continued through the treatment. This indicates that DHEA produced a $G_1$ block in HT-29 SF cells in a time- and dose-dependent manner.

Example 3

Analysis of Reversal of DHEA-mediated Growth Inhibition and Reversal of DHEA-induced Cell Cycle Arrest Reversal of DHEA-mediated Growth Inhibition. Cells were plated as above, and after 2 days received either 0 or 25 μM DHEA-containing medium supplemented with mevalonic acid ("MVA"; 2 mM), squalene ("SQ"; 80 μM), cholesterol ("CH"; 15 μg/ml), MVA plus CH, ribonucleosides ("RN"; uridine, cytidine, adenosine, and guanosine at final concentrations of 30 μM each), deoxyribonucleosides ("DN"; thymidine, deoxycytidine, deoxyadenosine and deoxyguanosine at final concentrations of 20 μM each), RN plus DN, or MVA plus CH plus RN, or medium that was not supplemented. All compounds were obtained from Sigma Chemical Co. (St. Louis, Mo.). Cholesterol was solubilized in ethanol immediately before use. RN and DN were used in maximal concentrations shown to have no effects on growth in the absence of DHEA.

Figure 3A:
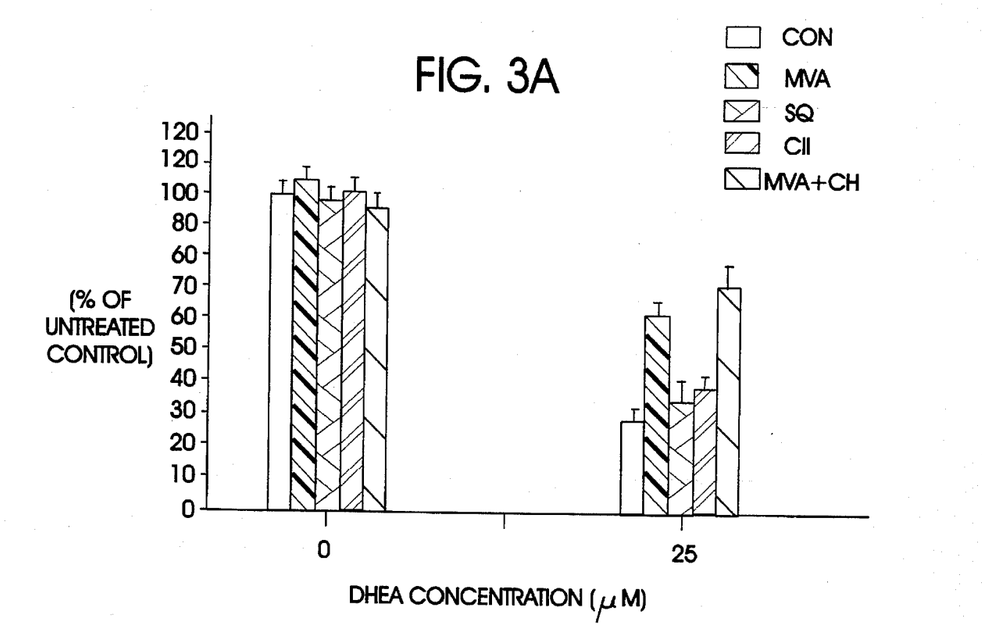
FIGS. 3A and 3B illustrate the reversal of DHEA-induced growth inhibition in HT-29 SF cells.
Figure 3B:
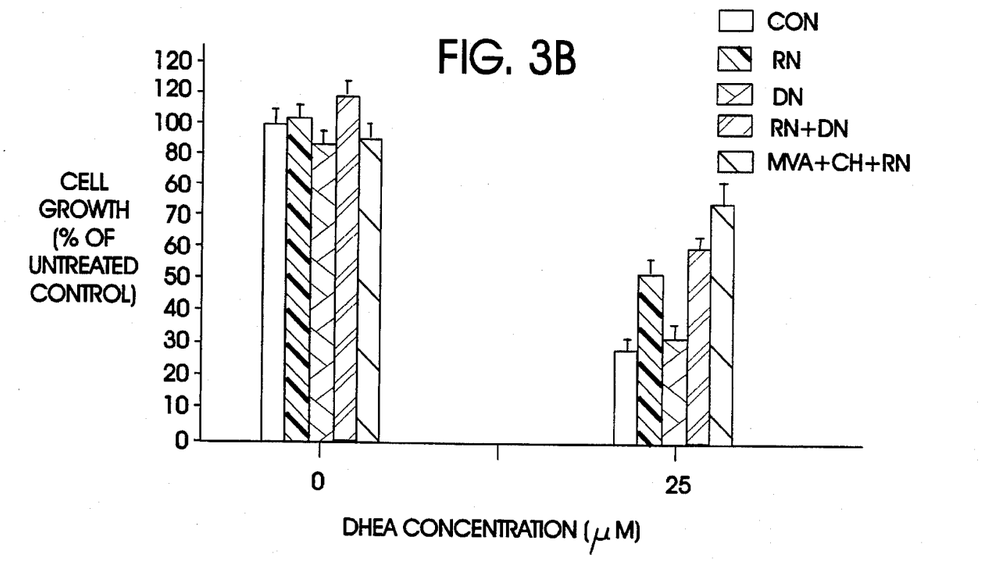
Figure 4A:
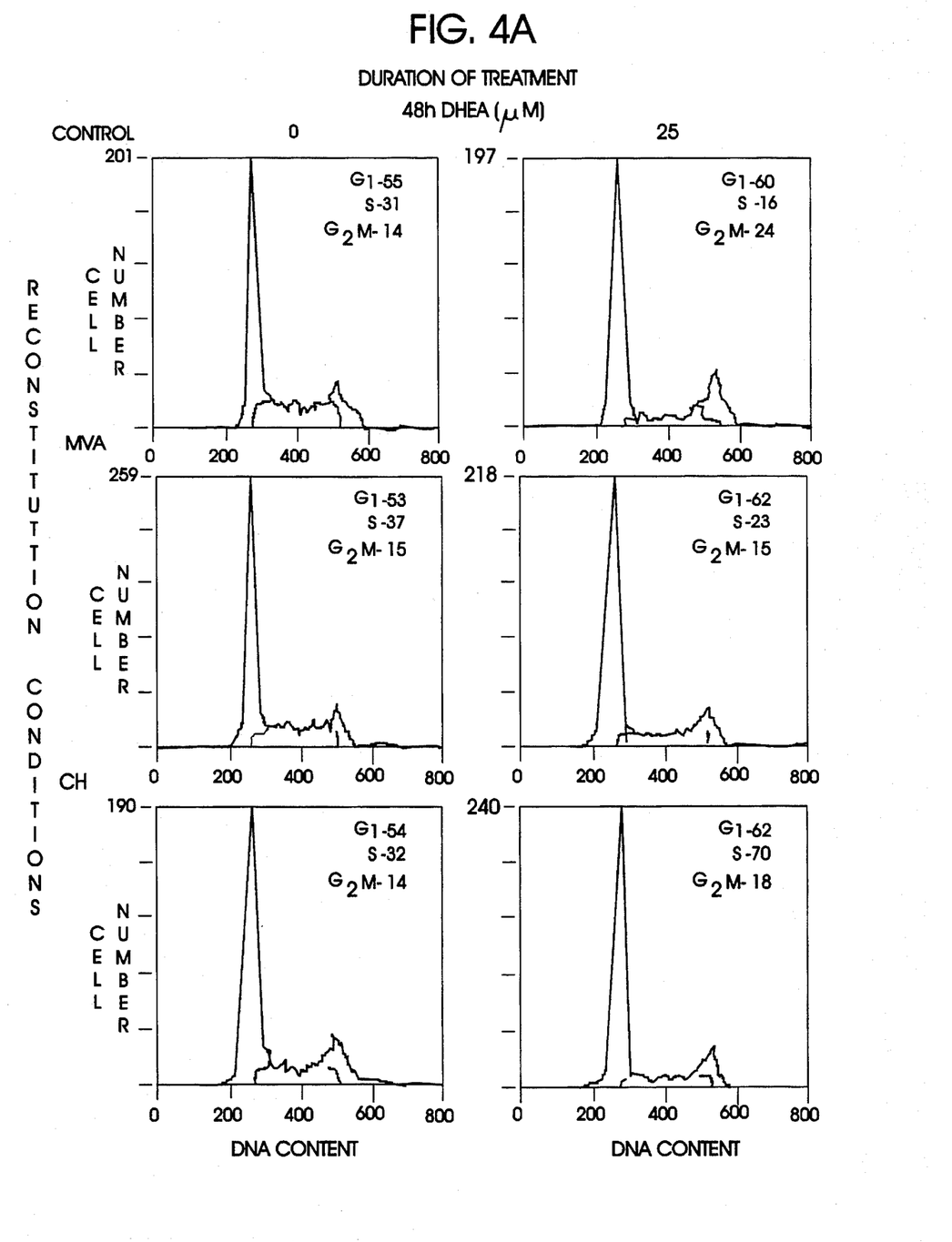
FIG. 4 illustrates the reversal of DHEA-induced $G_1$ arrest in HT-29 SF cells.
Figure 4B:
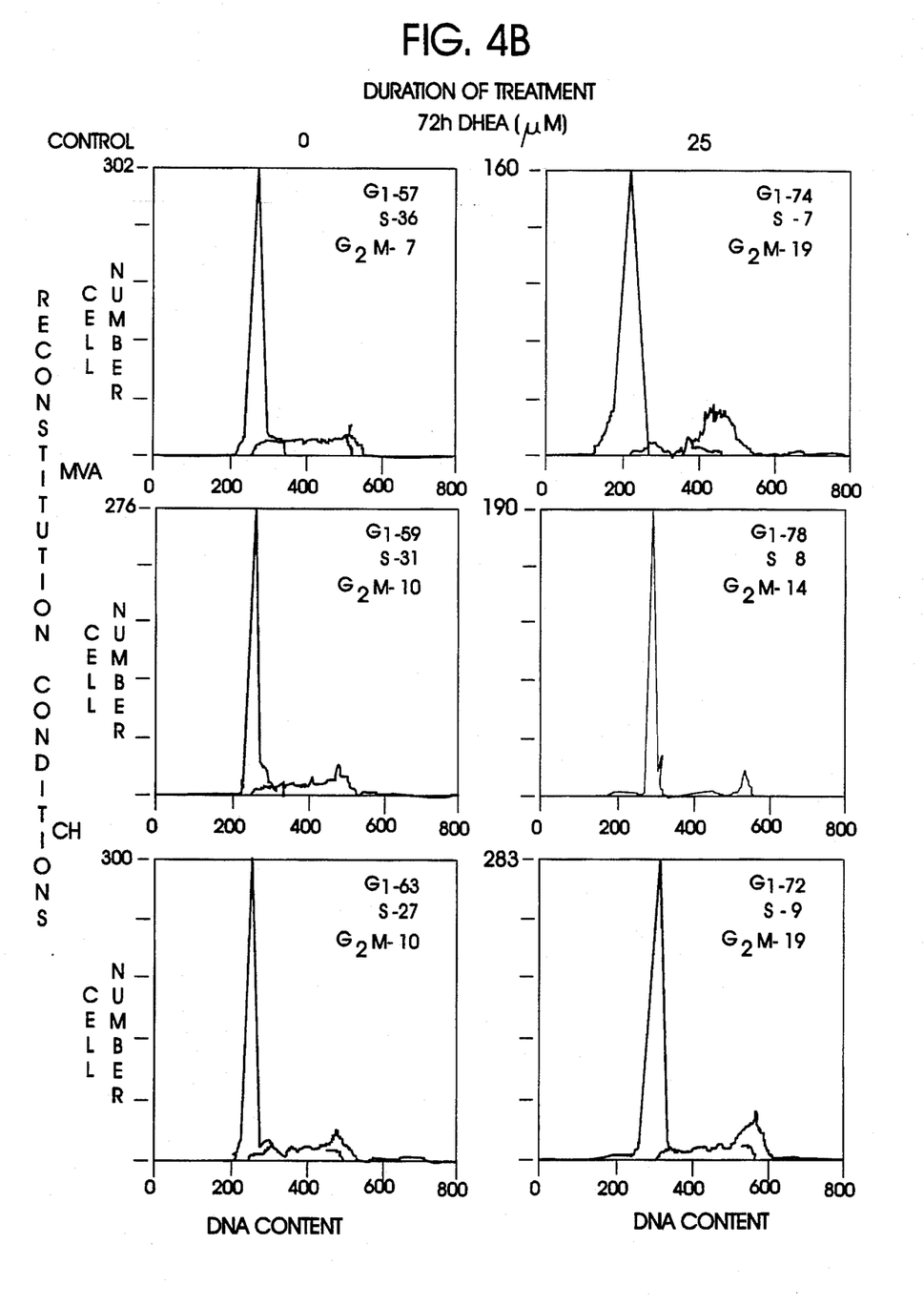
Figure 4C:
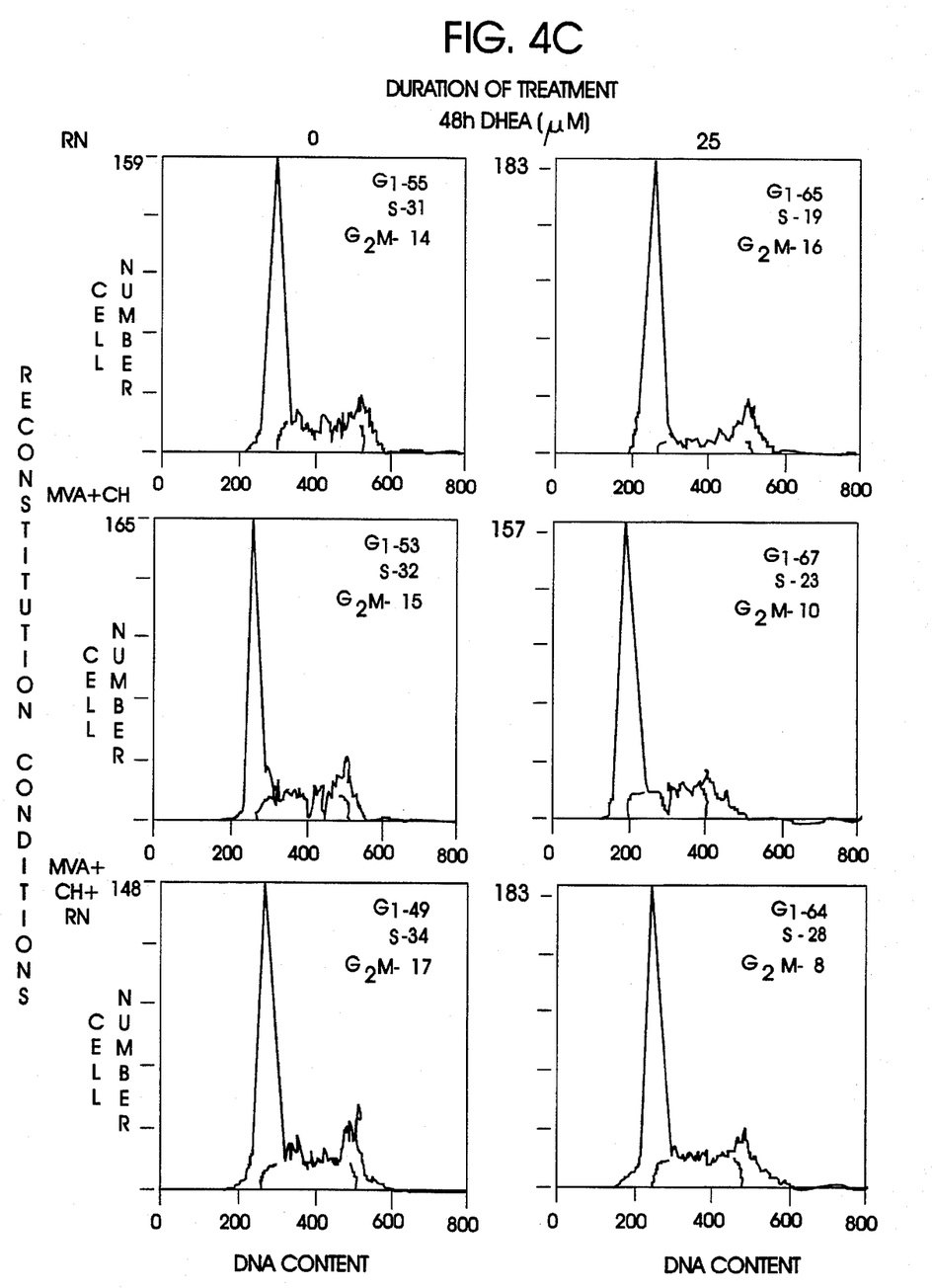
Figure 4D:
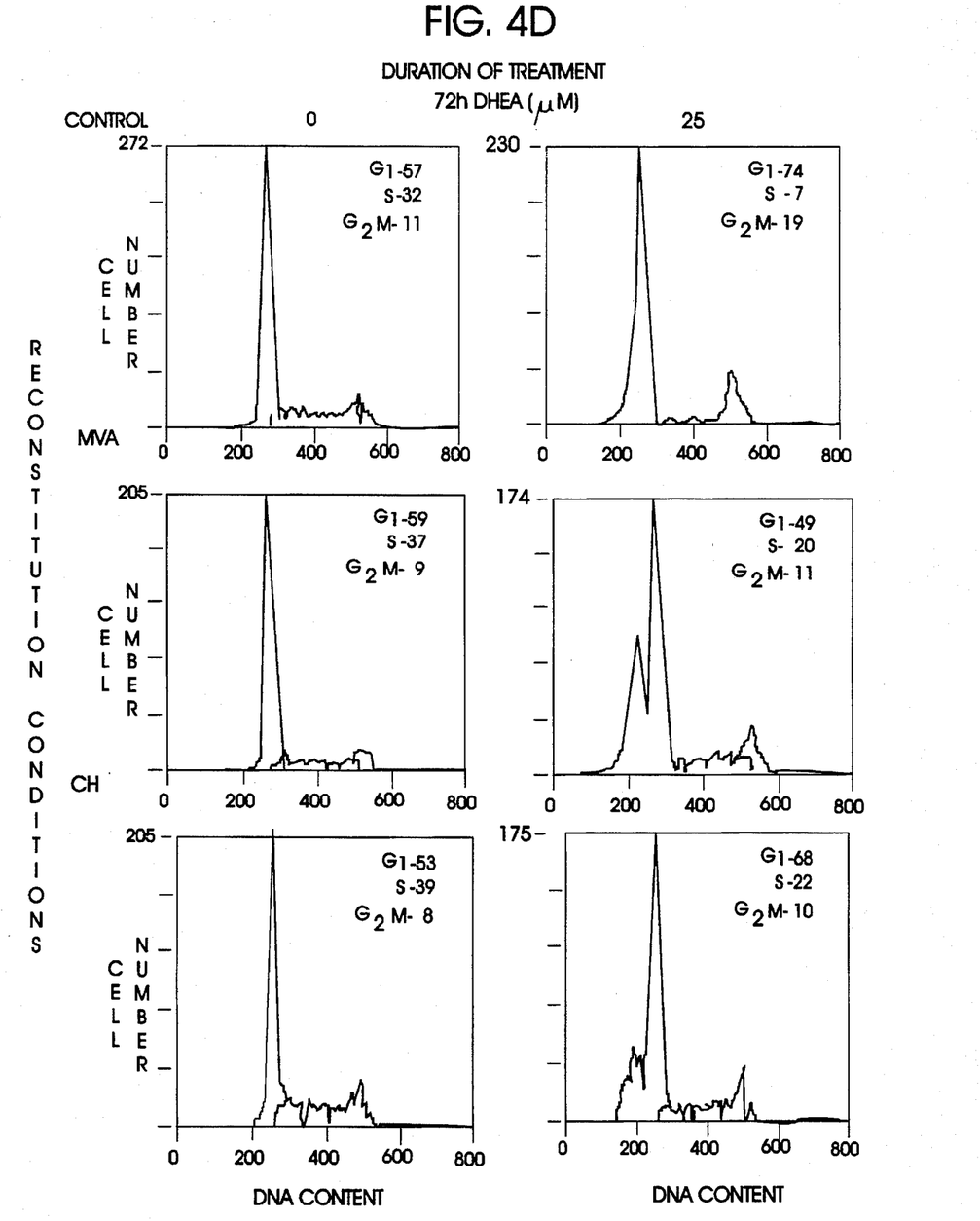

FIG. 3 illustrates the reversal of DHEA-induced growth inhibition in HT-29 SF cells. In A, the medium was supplemented with 2 μM MVA, 80 μM SQ, 15 μg/ml CH, or MVA plus CH (MVA+CH) or was not supplemented (CON). In B, the medium was supplemented with a mixture of RN containing uridine, cytidine, adenosine, and guanosine in final concentrations of 30 μM each; a mixture of DN containing thymidine, deoxycytidine, deoxyadenosine and deoxyguanosine in final concentrations of 20 μM each; RN plus DN (RN+DN); or MVA plus CH plus RN (MVA+CH+RN). Cell numbers were assessed before and after 48 hours of treatment, and culture growth was calculated as the increase in cell number during the 48 hour treatment period. Columns represent cell growth percentage of untreated controls; bars represent SEM. Increase in cell number in untreated controls was 173,370±6518. Each data point represents quadruplicate dishes from four independent experiments. Statistical analysis was performed using Student's t test. *, P<0.01; **, P, 0.001; compared to treated controls. Note that supplements had little effect on culture growth in absence of DHEA.

Under these conditions, the DHEA-induced growth inhibition was partially overcome by addition of MVA as well as by addition of MVA plus CH. Addition of SQ or CH alone had no such effect. This suggests that the cytostatic activity of DHEA was in part mediated by depletion of endogenous mevalonate and subsequent inhibition of the biosynthesis of an early intermediate in the cholesterol pathway that is essential for cell growth. Furthermore, partial reconstitution of growth was found after addition of RN as well as after addition of RN plus DN but not after addition of DN, indicating that depletion of both mevalonate and nucleotide pools is involved in the growth-inhibitory action of DHEA. However, none of the reconstitution conditions including the combined addition of MVA, CH, and RN completely overcame the inhibitory action of DHEA, suggesting either cytotoxic effects or possibly that additional biochemical pathways are involved.

Reversal of DHEA-induced Cell Cycle Arrest. HT-29 SF cells were treated with 25 μM DHEA in combination with a number of compounds, including MVA, CH, or RN, to test their ability to prevent the cell cycle-specific effects of DHEA. Cell cycle distribution was determined after 48 and 72 hours using flow cytometry.

FIG. 4 illustrates reversal of DHEA-induced arrest in HT-29 SF cells. Cells were plated ($10^5$ cells/60 mm dish) and 48 hours later treated with either 0 or 25 μM DHEA. The medium was supplemented with 2 μM MVA; 15 μg/ml CH; a mixture of RN containing uridine, cytidine, adenosine, and guanosine in final concentrations of 30 μM; MVA plus CH (MVA+CH); or MVA plus CH plus RN (MVA+CH+RN) or was not supplemented. Cells were harvested after 48 or 72 hours, fixed in ethanol, and stained with propidium iodine, and the DNA content per cell was determined by flow cytometric analysis. The percentage of cells in $G_1$, S, and $G_2M$ phases were calculated using the Cellfit cell cycle profile analysis program. S phase is marked by a quadrangle for clarity. Representative histograms from duplicative determinations are shown. The experiment was repeated two times. Note that supplements had little effect on cell cycle progression in the absence of DHEA.

With increasing exposure time, DHEA progressively reduced the proportion of cells in S phase. While inclusion of MVA partially prevented this effect in the initial 48 hours but not after 72 hours, the addition of MVA plus CH was also able to partially prevent S phase depletion at 72 hours, suggesting a requirement of both MVA and CH for cell progression during prolonged exposure. The addition of MVA, CH, and RN was apparently most effective at reconstitution but still did not restore the percentage of S phase cells to the value seen in untreated control cultures. CH or RN alone had very little effect at 48 hours and no effect at 72 hours. Morphologically, cells responded to DHEA by acquiring a rounded shape, which was prevented only by the addition of MVA to the culture medium (data not shown). Some of the DNA histograms after 72 hours DHEA exposure in FIG. 4 also show the presence of a subpopulation of cells possessing apparently reduced DNA content. Since the HT-29 cell line is known to carry populations of cells containing varying numbers of chromosomes (68–72; ATCC), this may represent a subset of cells that have segregated carrying fewer chromosomes.

The examples above provide evidence that in vitro exposure of HT-29 SF human colonic adenocarcinoma cells to concentrations of DHEA known to deplete endogenous mevalonate results in growth inhibition and $G_1$ arrest and that addition of MVA to the culture medium in part prevents these effects. DHEA produced effects upon protein isoprenylation which were in many respects similar to those observed for specific 3-hydroxy-3-methyl-glutaryl-CoA reductase inhibitors such as lovastatin and compactin. Unlike direct inhibitors of mevalonate biosynthesis, however, DHEA mediates its effects upon cell cycle progression and cell growth in a pleiotropic manner involving ribo- and deoxyribonucleotide biosynthesis and possibly other factors as well.

The foregoing examples are illustrative of the present invention, and are not to be taken as restrictive thereof. The invention is defined by the following claims, with equivalents of the claims to be included therein.

That which is claimed is:

1. In a method of combatting cancer in a subject comprising administering to said subject dehydroepiandrosterone (DHEA) or an analog thereof in an amount effectiv e to combat cancer, wherein said cancer is sensitive to said DHEA or analog thereof, the improvement comprising administering to said subject a ubiquinone in an amount effective to combat heart failure induced by said DHEA or analog thereof, wherein said DHEA or analog thereof is represented by the formula:

wherein:
R is hydrogen or a halogen;
R$^1$ is hydrogen or an SO$_2$OM group where M is hydrogen, sodium, a sulphatide group a phosphatide group wherein each of R$^2$ and R$^3$, which may be the same or different, is a straight or branched chain alkyl radical of 1 to 14 carbon atoms, or a glucuronide group and the broken line represents an optional double bond, and the hydrogen atom at position 5 is present in the alpha or beta configuration or the compound comprises a mixture of both configurations; and
said ubiquinone represented by the formula:

wherein n=1 to 10.

2. The method according to claim 1 wherein said dehydroepiandrosterone or analog thereof is represented by Formula (I) wherein R is bromine, fluorine or chlorine, R$^1$ is hydrogen, and the double bond is present.

3. The method according to claim 1 wherein said dehydroepiandrosterone or analog thereof is 16-alpha-fluoroepiandrosterone.

4. The method according to claim 1 wherein n is an integer from 6 to 10.

5. The method according to claim 1 wherein n is 10.

6. A method according to claim 1, wherein said dehydroepiandrosterone or analog thereof is administered to said subject parenterally and said ubiquinone is administered to said subject parenterally.

7. A method of combatting cancer in a subject comprising administering to said subject dehydroepiandrosterone (DHEA) or an analog thereof in an amount effective to combat cancer, wherein said cancer is sensitive to said DHEA or analog thereof, concurrently with a ubiquinone in an amount effective to combat heart failure induced by said DHEA or analog thereof, said DHEA or analog thereof represented by the formula:

wherein:
R is hydrogen or a halogen;
R$^1$ is hydrogen or an SO$_2$OM group where M is hydrogen, sodium, a sulphatide group a phosphatide group wherein each of R$^2$ and R$^3$, which may be the same or different, is a straight or branched chain alkyl radical of 1 to 14 carbon atoms, or a glucuronide group and the broken line represents an optional double bond, and the hydrogen atom at position 5 is present in the alpha or beta configuration or the compound comprises a mixture of both configurations; and
said ubiquinone represented by the formula:

wherein n=1 to 10.

8. A method of combatting cancer in a subject comprising concurrently administering to said subject dehydroepiandrosterone (DHEA) or an analog thereof in an amount effective to combat cancer, wherein said cancer is sensitive to said DHEA or analog thereof, with a ubiquinone in an amount effective to combat heart failure induced by said DHEA or analog thereof, said DHEA or analog thereof represented by the formula:

wherein
R is a halogen;
R¹ is hydrogen; and
the broken line represents an optional double bond and the hydrogen atom at position 5 is present in the alpha or beta configuration or the compound comprises a mixture of both configurations; and
said ubiquinone represented by the formula:

wherein n=6 to 10.

9. The method according to claim 8, wherein said DHEA or analog thereof is 16-alpha-fluoroepiandrosterone and wherein n=10.

10. In a method of combatting cancer in a subject comprising administering to said subject dehydroepiandrosterone (DHEA) or an analog thereof in an amount effective to combat cancer, wherein said cancer is sensitive to said DHEA or analog thereof, the improvement comprising administering to said subject an ubiquinone in an amount effective to combat heart failure induced by said DHEA or analog thereof, wherein said DHEA or analog thereof is represented by the formula:

wherein
R is bromine, fluorine or chlorine;
R¹ is hydrogen; and
the double bond is present; and wherein said ubiquinone is represented by the formula:

wherein n=10.

11. In a method comprising administering to a subject dehydroepiandrosterone (DHEA) or an analog thereof in need of such treatment in a therapeutically effective amount, the improvement comprising administering to said subject a ubiquinone in an amount effective to combat heart failure induced by said DHEA or analog thereof, wherein said DHEA or analog thereof is represented by the formula:

wherein:
R is hydrogen or a halogen;
R¹ is hydrogen or an SO₂OM group where M is hydrogen, sodium, a sulphatide group a phosphatide group wherein each of R² and R³, which may be the same or different, is a straight or branched chain alkyl radical of 1 to 14 carbon atoms, or a glucuronide group and the broken line represents an optional double bond, and the hydrogen atom at position 5 is present in the alpha or beta configuration or the compound comprises a mixture of both configurations; and
said ubiquinone represented by the formula:

wherein n=1 to 10.

12. A method according to claim 11, wherein R is bromine, fluorine, or chlorine; R¹ is hydrogen; and the double bond is present; and wherein n=10.

13. A pharmaceutical formulation comprising dehydroepiandrosterone (DHEA) or an analog thereof in an amount effective to combat cancer, wherein said cancer is sensitive to said DHEA or analog thereof, and a ubiquinone in an amount effective to combat heart failure induced by said DHEA or analog thereof in a pharmaceutically acceptable carrier, wherein said DHEA or analog thereof is represented by the formula:

(I)

wherein:

R is hydrogen or a halogen;

$R^1$ is hydrogen or an $SO_2OM$ group where M is hydrogen, sodium, a sulphatide group a phosphatide group wherein each of $R^2$ and $R^3$, which may be the same or different, is a straight or branched chain alkyl radical of 1 to 14 carbon atoms, or a glucuronide group and wherein the broken line represents an optional double bond, and the hydrogen atom at position 5 is present in the alpha or beta configuration or the compound comprises a mixture of both configurations; and said ubiquinone represented by the formula:

(II)

wherein n=1 to 10.

14. A pharmaceutical formulation according to claim 11 wherein said DHEA or analog thereof is represented by Formula I, wherein R is bromine, fluorine, or chlorine, and $R^1$ is hydrogen, and the double bond is present.

15. A pharmaceutical formulation according to claim 11 wherein said DHEA or analog thereof is 16 alpha-fluoroepiandrosterone.

16. A pharmaceutical formulation according to claim 11 wherein said ubiquinone is represented by Formula II, wherein n is an integer from 6 to 10.

17. A pharmaceutical formulation according to claim 11 wherein said ubiquinone is represented by Formula II, wherein n is 10.

18. A pharmaceutical formulation according to claim 12 wherein said pharmaceutically acceptable carrier is an aqueous carrier.

19. A pharmaceutical formulation according to claim 13 wherein said pharmaceutically acceptable carrier is a solid carrier.

* * * * *

UNITED STATES PATENT AND TRADEMARK OFFICE
CERTIFICATE OF CORRECTION

PATENT NO. : 5,527,789
DATED : June 18, 1996
INVENTOR(S) : Jonathan W. Nyce

It is certified that error appears in the above-identified patent and that said Letters Patent is hereby corrected as shown below:

In column 1, after line 7, please insert the following new paragraph:
--This invention was made with Government support under Grant No. CA47217, awarded by the National Cancer Institute. The Government has certain rights in the invention.--

In column 2, line 61, "SO2OM" should be --$SO_2OM$--.

Signed and Sealed this

Twenty-fourth Day of June, 1997

Attest:

BRUCE LEHMAN

Attesting Officer

Commissioner of Patents and Trademarks